United States Patent
Gramann et al.

(10) Patent No.: US 9,775,691 B2
(45) Date of Patent: Oct. 3, 2017

(54) SYSTEM AND DEVICE FOR DISPENSING A DENTAL MATERIAL AND A CARTRIDGE FOR USE WITH THE SYSTEM OR DEVICE

(71) Applicant: 3M INNOVATIVE PROPERTIES COMPANY, St. Paul, MN (US)

(72) Inventors: Jens Gramann, Gräfelfing (DE); Korbinian Schepke-Gerlach, Gauting (DE); Manfred Harre, Landsberg am Lech (DE); Emir Jelovac, Munich (DE); Ralf Kelz, Germering (DE); Özcan Dönmez, Landsberg am Lech (DE); Christian A. Richter, Feldafing (DE)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 183 days.

(21) Appl. No.: 14/411,655

(22) PCT Filed: Jun. 27, 2013

(86) PCT No.: PCT/US2013/048104
§ 371 (c)(1),
(2) Date: Dec. 29, 2014

(87) PCT Pub. No.: WO2014/008082
PCT Pub. Date: Jan. 9, 2014

(65) Prior Publication Data
US 2015/0157429 A1    Jun. 11, 2015

(30) Foreign Application Priority Data
Jul. 3, 2012   (EP) .................................... 12174834

(51) Int. Cl.
*B67D 7/14*        (2010.01)
*A61C 9/00*        (2006.01)
(Continued)

(52) U.S. Cl.
CPC ........ *A61C 9/0026* (2013.01); *B05C 11/1002* (2013.01); *B05C 17/00566* (2013.01);
(Continued)

(58) Field of Classification Search
CPC ....... A61C 5/064; A61C 5/068; A61C 9/0026; B05C 11/1002; B05C 11/10;
(Continued)

(56) References Cited

U.S. PATENT DOCUMENTS 5,054,655 A     10/1991  Keller
6,315,164 B1 *  11/2001  Muhlbauer ............ A61C 5/064
                                                    222/325
(Continued)

FOREIGN PATENT DOCUMENTS

| DE | 102006043710 | 3/2008 |
|----|--------------|--------|
| DE | 102009049286 | 5/2011 |
| EP | 0699582      | 3/1996 |
| WO | 00/38841     | 7/2000 |
| WO | 2005/117741  | 12/2005 |
| WO | 2007/121003  | 10/2007 |

OTHER PUBLICATIONS

International Search Report for PCT International Application No. PCT/US2013/048104, mailed on Sep. 26, 2013, 4 pages.

*Primary Examiner* — Patrick M Buechner

(57) ABSTRACT

A system for dispensing a dental material comprises a cartridge from which the dental material is extrudable. The cartridge comprises a operating means and an interface for transmitting a cartridge output based on a user input. The system further has a dental dispensing device having a receptacle for receiving the cartridge and an interface for receiving the cartridge output. The system helps maximizing reliability and maximizing safety in operation for dispensing dental material.

11 Claims, 9 Drawing Sheets

(51) Int. Cl.
  *B05C 17/01* (2006.01)
  *B05C 17/005* (2006.01)
  *B05C 11/10* (2006.01)
  *B05B 12/00* (2006.01)
  *B05C 17/015* (2006.01)
  *A61C 5/64* (2017.01)

(52) U.S. Cl.
  CPC .... B05C 17/00596 (2013.01); B05C 17/0103 (2013.01); B05C 17/0116 (2013.01); *A61C 5/64* (2017.02); *B05B 12/002* (2013.01); *B05C 17/015* (2013.01)

(58) Field of Classification Search
  CPC ........ B05C 17/00566; B05C 17/00596; B05C 17/0103; B05C 17/015; B05C 17/0116; B05B 12/002
  See application file for complete search history.

(56) References Cited

U.S. PATENT DOCUMENTS

| | | | |
|---|---|---|---|
| 6,500,001 B2* | 12/2002 | Horth | A61C 5/062 366/142 |
| 8,394,105 B2* | 3/2013 | Vendrely | A61B 17/8833 606/92 |
| 2002/0064754 A1* | 5/2002 | Horth | A61C 5/062 433/80 |
| 2003/0022128 A1* | 1/2003 | Heymann | A61C 5/064 433/89 |
| 2007/0158362 A1* | 7/2007 | Muller-Paul | A61C 5/062 222/137 |
| 2008/0173673 A1 | 7/2008 | Müller-Paul | |
| 2013/0115568 A1* | 5/2013 | Jelovac | A61C 5/064 433/36 |

\* cited by examiner

SYSTEM AND DEVICE FOR DISPENSING A DENTAL MATERIAL AND A CARTRIDGE FOR USE WITH THE SYSTEM OR DEVICE

FIELD OF THE INVENTION

The invention relates to a system for dispensing a dental material, a cartridge and a dental dispensing device of the system. In particular the invention relates to a system in which operating means for user operation of the device are arranged on the cartridge.

BACKGROUND ART

In dentistry a variety of devices are available which allow for preparation and/or application of dental materials in a dentist's practice. In particular for preparation of materials that are typically used at larger amounts, like for example dental impression materials, devices have been developed that provide for automatic dispensing from packages and/or for mixing of such materials. An exemplary device for mixing and dispensing a dental impression material is for example available under the designation 3M™ ESPE™ Pentamix™ from 3M ESPE AG, Germany. Typically such a device allows for two material components to be simultaneously supplied from a package through a mixer where they are mixed. Often the devices provide for continuously extruding the components through a mixer, where the components are mixed as the components flow through the mixer and released from an outlet. The dental materials are typically provided in containers that can be replaceably received in the devices. Thus the same device can be refilled with fresh material by exchange of the containers and can further be used different types of dental materials.

There are devices which can be adjusted for dispensing the dental materials at desired parameters, for example a desired dispensing speed and/or mixing speed. Some devices have functionality to recognize the material inserted in the device and to automatically adjust appropriate operation parameters.

For example WO 2000/38841 discloses a device for discharging a flowable material from a container using a motor-driven discharging device. The device is adapted for detecting information about a correct placement of the container in the device, about the date of expiry and/or about the viscosity, for example. The container can be provided with a transponder so that, when the container is correctly positioned in the device, the transponder co-operates with an interrogator unit which releases and/or controls the device according to the information detected.

WO 2007/121003 discloses a dispenser for dental material. The dispenser has plungers driven by a first drive and a dynamic mixer driven by a second drive. The dispenser is adapted controlling the first and/or second drive for advancing and mixing the dental material at a predetermined, non-uniform drive speed profile. The dispenser has a sensor for identifying the dental material to be advanced and mixed, and to automatically select a speed profile according to the dental material identified by the sensor.

Although existing solutions provide certain advantages there is still a desire for a system for dispensing dental materials which can dispense and mix different types of dental materials, which is relatively safe and reliable in use and which helps minimizing costs.

SUMMARY OF THE INVENTION

The invention in one aspect relates to a system for dispensing a dental material, for example a dental impression material provided in the form of two individual components that are mixed by the system to form the dental impression material. The system comprises a cartridge from which the dental material is extrudable. The cartridge comprises operating means and an interface for providing a cartridge output that is based on a user input sensed through the operating means. The operating means comprises a contact based sensor or a contactless (or non-contact) sensor. The system further comprises a dental dispensing device which has a receptacle for the cartridge and at least one piston for extruding the dental material from the cartridge. The device has an interface for detecting the cartridge output. For recognition of the cartridge output the device interface comprises a contactless sensor or contact switch.

The invention is advantageous in that it helps maximizing the reliability and safety of a dental material dispensing device. For example a frequently used manually operated operating means for controlling the device may be present on the cartridge and thus may be easily replaceable with the cartridge. Malfunctions due to hardenable dental material eventually affecting the operation of the operating means may be minimized Further the invention allows for easily blocking certain operations of the device in a situation in which no cartridge is placed in the device. This may for example prevent a user from causing the plungers to move forward into the empty receptacle. Because the plungers may be operated at relatively high forces blocking such operation may help maximizing safety.

The term operating means for the purpose of this specification is preferably understood as any technical appliance which is suitable to detect a physical interaction between a user and the appliance and to convert the interaction into a machine processible physical quantity. The term operating means thus is not limited to individual embodiments disclosed herein but also encompasses other embodiments according to the common technical knowledge of the person skilled in the art.

In one embodiment a movable actuator forms a preferred contact based sensor in the sense of the present invention. Such a movable actuator may be formed by a movable button, finger plate or lever, for example. However other contact based sensors may be used which do not have any movable parts but are suitable to detect a contact, for example between a user and a surface of the operating means. In one example a touch panel or touch pad based on capacitive, resistive, inductive or optical detection may be used.

In a further embodiment a contactless sensor may for example comprise an electrically driven optical sensor. The operating means may further comprise a non-contact based or contactless transmitter. A contactless transmitter may comprise a reflector which cooperates with an optical sensor in the device. In the latter case the optical sensor may monitor a light beam sent on the reflector and reflected to the sensor. A user input may be provided by interruption of that light beam and thus detected by the sensor. Another transmitter may be formed by a light guide that guides a light signal between two ends of the light guide, with one end cooperating with a light sensor in the device and the other end being exposed at the cartridge for user interaction.

In one embodiment the operating means is adapted to convert the user input to the operating means into the cartridge output. The system may be particularly adapted to convert the user input into a position of a mechanical element. Accordingly the cartridge output may be represented by the position of the mechanical element. The mechanical element is preferably movable between at least two positions which may be detectable by the dental dispensing device.

In one embodiment the mechanical element is formed by a rod which is mechanically coupled with an actuator such that a movement of the actuator, for example by a user, also causes a movement of the rod. Thus a user input in the form of an actuation of the actuator is converted in a positioning of the rod. The rod may be formed in a single piece with the actuator or attached thereto. For example the actuator may be in the form of a pivotable finger plate from which the rod extends, for example along a generally circular path about the pivot. Alternatively the actuator may be in the form of a finger plate or button and the rod may be mechanically connected to the actuator via one or more pivots or any other suitable transmission.

In a further embodiment the mechanical element is formed by the actuator. For example the actuator may be a movable lever or movable button which is adapted for positioning by a user and the position of the lever or button may be directly used as the cartridge output.

In one embodiment the cartridge output comprises a contactless signal. The signal may be provided in the form of light or a magnetic field, and different states of the signal may be represented by different intensities of the light or a magnetic field.

Generally placing a cartridge in the receptacle of the device preferably establishes an interconnection between the cartridge interface and the device interface. In the interconnected state of the cartridge and device interface the system is enabled such that the cartridge output can be detected by the device.

In one embodiment the device is adapted to control an operation of the device dependent on the cartridge output and thus also dependent on the user input. In particular the device is preferably adapted to control at least two different operation modes (or one operation mode and an off mode) of the device dependent on a user input in a situation in which the cartridge is placed in the receptacle of the device. For example absence of a user input may cause the device to operate in a first operation mode or to not operate, and a user input may cause the device to operate in a second operation mode. A further user input may cause the device to reset in the first operation mode or to switch off. The user input preferably is independent from a movement of the cartridge relative to the device. Further the cartridge and the device preferably remain in generally the same position relative to each other during a user input, for example during the actuator moves. The device is preferably adapted to detect the cartridge output via the device interface and to control the device based on the cartridge output.

In one embodiment the system is adapted such that in a situation in which the cartridge is received in the receptacle of the device, the contact switch and the mechanical element are arranged for cooperation with one another. For example a user input may be converted in a positioning of the mechanical member from a first toward a second position. The contact switch and the mechanical member are preferably arranged relative to each other such that in the first position of the mechanical member the contact switch is inactivated and in the second position of the mechanical member the switch is activated. The device may be adapted such that the operation of the device can be started and stopped dependent on the cartridge output. For example in the activated stage of the switch an electric circuit may be closed which causes a motor of the device to operate, whereas in the inactivated stage the motor is switch off. The skilled person will recognize that equivalent solutions can be implemented by a switch which is activated in the first position and inactivated in the second position. Further in the inactivated stage of the switch the electric circuit may be closed and in the activated stage the motor may be switched off.

In one embodiment the cartridge output comprises an encoded output and the device interface comprises a sensor for recognizing the encoding For example the cartridge may comprise an actuator having a surface exhibiting an encoding in the form of different colors and/or shapes (like a bar code and/or pin code), and the device may have a sensor for recognizing the encoding. The encoding may be used to operate the device at different operation modes depending on the cartridge placed in the device. This enables the use of different cartridges filled with different dental materials in the same dental dispensing device at customized operation modes of the device for each dental material. The device may further be adapted such that upon a user input which initiates a dispensation of the dental material recognition of the encoding is also initiated. This may help maximizing the reliability of the system in that the encoding is verified short before dispensation of the material.

In one embodiment the device further comprises at least one plunger and a drive for driving the plunger by motor power. The drive may comprise a mechanical clutch which can be switched for selectively establishing or interrupting a transmission between the motor and the plunger. In one example the device has a motor driven spindle drive, having a combination of a spindle and a clasp nut, for driving the plunger. The clasp nut and the spindle may be adapted such that they can be selectively engaged or disengaged and thus also form the mechanical clutch. However the device may further have a geared connection between the plunger and the motor, and a mechanical clutch may be arranged to selectively establish or interrupt that geared connection.

In one embodiment the system is adapted such that the cartridge output can be further used to switch the clutch. Accordingly the same or an additional cartridge output may cause a member of the clutch to move and thus to establish or interrupt the transmission between the motor and the plunger. In a particular embodiment the actuator is mechanically coupled with the mechanical element and, in a situation in which the cartridge is placed in the receptacle of the device, the mechanical element is further mechanically coupled with the clutch member. In this particular embodiment the mechanical element is further mechanically coupled with a sensor or switch in the device for controlling an operation of the device, preferably for switching the motor on and off.

In one embodiment the system is adapted such that a user input causes activating the motor and switching the clutch timely subsequently. For example the system may be adapted such that upon actuating (for example moving) the actuator the mechanical member first actuates the switch and subsequently urges the clutch member (for example the clasp nut) toward an engagement with another clutch member (for example toward the spindle). This preferably helps the clutch members to easily engage and help avoiding a static situation in which per se matable structures of the clutch are misaligned and prevent mating of the structures. For example the ridges of the threads of the spindle and the clasp nut may in certain rotational positions relative to each other be co-aligned and block the spindle and clasp nut from engaging. A rotation of one of the spindle and the clasp nut in this case helps resolving such a situation.

In a further embodiment the device comprises two plungers, each for extruding one component from the cartridge. The plungers are preferably adapted or restricted for extruding both components simultaneously from the cartridge. The device may further comprise a motor driven drive shaft for driving a dynamic mixer. Such a dynamic mixer preferably has in a mixing chamber a mixing rotor which is connectable to the drive shaft of the device for driving the mixing rotor. Further the mixer is preferably connectable to component chambers of the cartridge. Thus the components may be extruded into the mixer and may be mixed as they flow through the mixing chamber toward an outlet of the mixer.

The invention in a further aspect relates to a cartridge for holding a dental material for extrusion by a dental dispensing device. The cartridge comprises operating means for sensing a user input and a cartridge interface for transmitting a cartridge output that is based on the user input.

In one embodiment the operating means comprises a movable button. The button may comprise a rod which is mechanically coupled with the button such that a movement of the button also causes a movement of the rod. The rod may form one piece with the button or may be connected, for example via one or more pivots and/or slide transmissions, the button. The button preferably has a finger surface on which a user may place the finger for pressing the button. The button is preferably arranged within the cartridge such that the finger surface of the button is exposed at an outer surface of the cartridge. Thus a user may easily access the button.

In one embodiment the button is arranged for a linear or pivotable movement within the cartridge. The rod or the button underside of the finger surface may be accessible from a surface of the cartridge laterally or opposite of the button surface. Accordingly the cartridge placed in the dental dispensing device preferably provides the finger surface of the button accessible to a user and a transmission of a button's actuation internally within the system, preferably blocked from user access.

The invention in a further aspect relates to a dental dispensing device, having a receptacle for receiving a cartridge from which a dental material can be extruded. The dental dispensing device may have at least one piston, preferably two pistons, for extruding the dental material from the cartridge. The device preferably has an interface for receiving a cartridge output from a cartridge interface. The device is preferably adapted to operate depending on the cartridge output, for example may be switched on and/or off in response to the cartridge output. The interface is preferably arranged within the receptacle of the device. Accordingly the interface is covered (in particular not accessible be a user) by a cartridge placed in the receptacle. The device thus is preferably operable by a user input sensed on operating means of the cartridge and the cartridge output transmitted to the device based on the user input.

In one embodiment the operating means is a user operable start/stop button of the cartridge and the device does not have any user operable start/stop button. This means that although the device may have further switches or buttons the dispensation of dental material may only be initiated and/or terminated by operation of the start/stop button of the cartridge. Further in this regard a user operable button for the purpose of this specification is regarded as button which is directly accessible to a user of the system in which a cartridge is placed in the receptacle of the device.

DETAILED DESCRIPTION OF THE INVENTION

Figure 1:
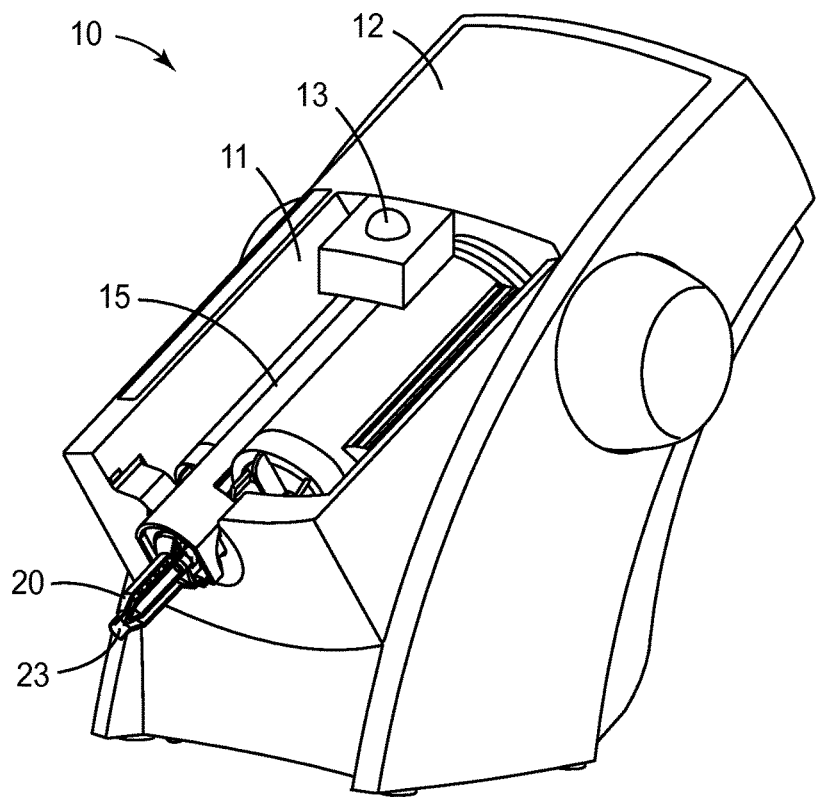
FIG. 1 is a perspective view of a system comprising a cartridge and a device according to an embodiment of the invention.
Figure 2:
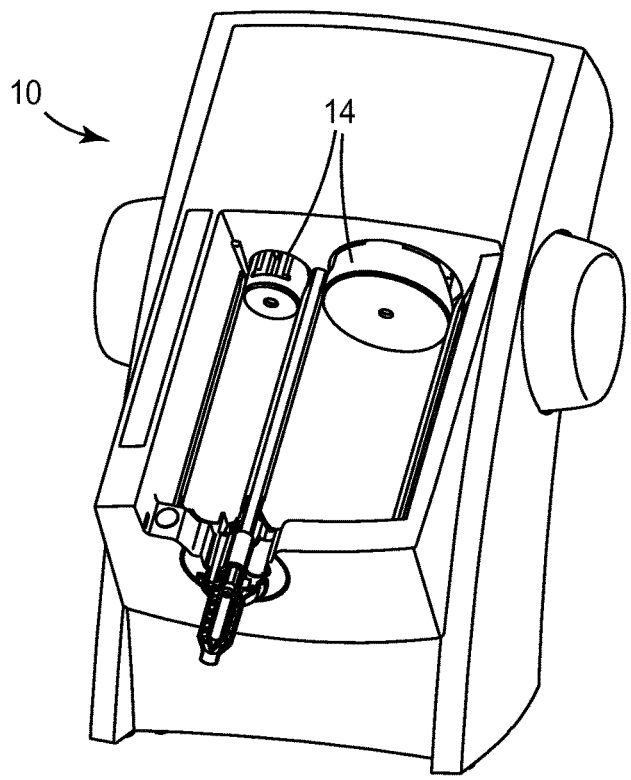
FIG. 2 is a perspective view of the device shown in FIG. 2 without the cartridge.

FIG. 1 shows a system 10 for dispensing dental materials. The system 10 comprises a dental dispensing device 12 which is adapted for receiving a cartridge 15 in which the material, preferably in the form of two separate components, is provided. The cartridge 15 is preferably removably received in a dedicated receptacle 11 of the device 12. The system 10 further has attached thereto a mixer 20 for mixing the components. The material components are preferably provided in the cartridge in separate containers from which the components can be extruded into the mixer 20 by movement of plungers 14 (shown in FIG. 2) of the device 12. The skilled person will recognize that in some embodiments the containers may be removably received in the cartridge, whereas in other embodiments the containers may form part of the cartridge. In the first case (as illustrated) the cartridge 15 may be reusable and adapted to hold and position the containers relative to the plungers of the device. The containers, for example foil bags (not visible) having outlets, may be compressed for extruding the material components by moving the plungers into the cartridge. Such a cartridge is disclosed for example in WO 2005/127741. In the latter case the material components may be directly contained within the cartridge and may be extruded therefrom by pushing cartridge pistons forward via moving the plungers into the cartridge. According to the invention the cartridge comprises operating means 13 (for example a button) for sensing a user input, and the user input may be used in controlling an operation of the device. The system 10 is further adapted to convey or transmit such a user input from the cartridge 15 to the device 12 (as explained in more detail in the following), for example to start and/or stop extrusion of the dental material.

The mixer 20 is connected with the containers such that the individual components can be advanced into a mixing chamber of the mixer 20 where the components can be mixed, for example by help of a rotating mixing rotor which causes the components to merge to form a mixture. The mixture can exit through an outlet 23 of the mixer 20. The system 10 shown may be used to mix and dispense a hardenable dental impression material, for example. Mixed dental impression material may for example be used to fill a dental tray which is then placed into a patient's mouth for taking a dental impression. The mixer 20 of the system 10 shown is replaceably attached at the system 10. Therefore when the mixed material hardens and thus blocks the mixer the used mixer may be replaced by an unused mixer for the next use of the system 10. A similar system and device is available under the designation 3M™ ESPE™ Pentamix™ from 3M ESPE AG, Germany.

Figure 3:
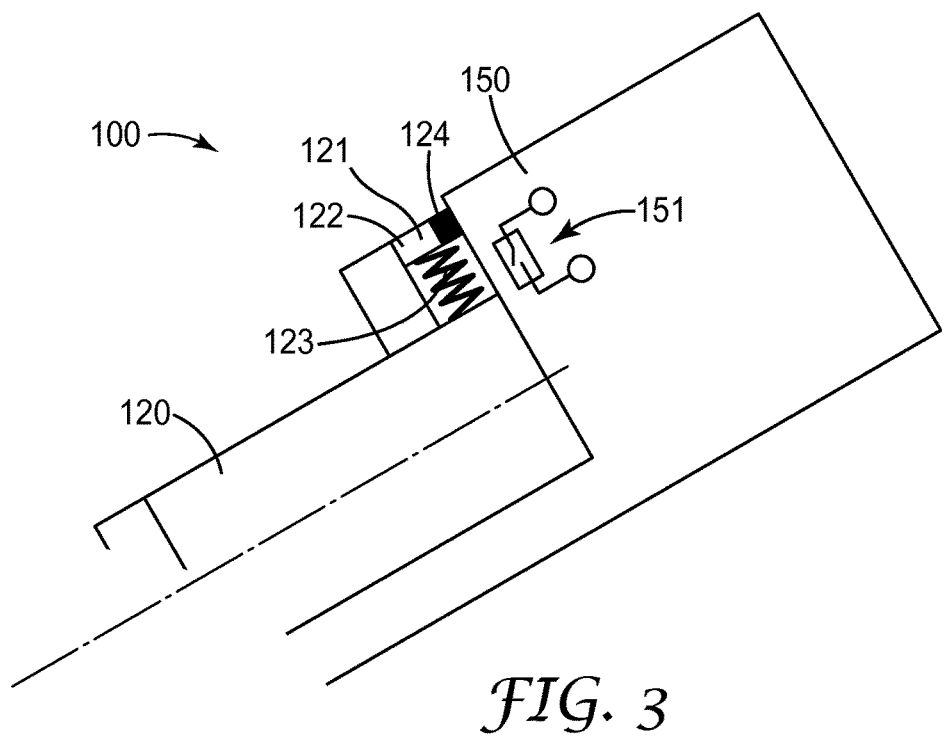
FIG. 3 is a schematic side view of a system according to an embodiment of the invention.

FIG. 3 shows an example of a system 100 for dispensing a dental material. The system 100 generally corresponds to the system illustrated in FIGS. 1 and 2 although it is illustrated more schematically in some respects in this Figure. In addition the system 100 as illustrated shows further details relating to the particular example. The system 100 comprises a dental material dispensing device 150 and a cartridge 120. The cartridge 120 is removably placed in the device 150. Further the cartridge 120 comprises operating means 121 for sensing a user input. In the example the operating means 121 comprise a button 122 which is suspended within the cartridge 120 for a movement between an inactivated position (shown in FIG. 3) and an activated position (shown in FIG. 4). The operating means 121 may be adapted for resetting in one of the inactivated or activated position (for example as shown in the inactivated position). Alternatively the operating means may be adapted for positioning and resting in both, the activated and inactivated position (not shown). In the example a spring 123 urges the button 122 toward the inactivated position. Accordingly a user may press the button 122 against the spring load toward the activated position, and the spring 123 may reset the button 122 automatically upon release.

The button 122 comprises a magnetic element 124 and the device 150 has a reed switch 151 for cooperation with the magnetic element 124. The reed switch 151 is generally adapted to switch, for example close or interrupt an electric circuit or contact, upon a change of a magnetic field in the vicinity of the reed switch. In the illustrated example the reed switch 151 is a so-called NOC (normally open contact) switch, which interrupts an internal electric conductor if it is not exposed to a magnetic field or if it is exposed to a magnetic field which strength is below a predetermined threshold. The illustrated reed switch 151 further closes the contact if it is exposed to a magnetic field of strength above a predetermined threshold. In the situation illustrated in FIG. 3 the button 122 is in the inactivated position, and accordingly the magnetic element 124 is in a remote position relative to the reed switch 151 in the device 150. In the remote position of the magnetic element 124 the strength of the magnetic field acting on the reed switch 151 is below the predetermined threshold so that the reed switch 151 opens the contact. Upon moving the button 122 toward the activated position the magnetic element 124 approaches the reed switch 151 so that the strength of the magnetic field acting on the reed switch 151 increases. Once the magnetic element 124 is sufficiently close to expose the reed switch 151 with a magnetic field of a strength above the predetermined threshold the reed switch 151 closes the contact. Thus a contactless interface between the cartridge 120 and the device 150 is provided. Further in the example the interface is adapted for transmitting—in this particular example via a magnetic field—a contactless cartridge output that is based on the user input to the device. Accordingly the system 100 is adapted such that a user input on the operating means 121 of the cartridge 120 causes the magnetic element 124 to move relative to the reed switch 151 in the device 150, and the resulting change of the magnetic field from the magnetic element 124 on the reed switch 151 triggers the reed switch 151 to switch.

The skilled person will recognize that the same function is achieved by use of a metal element instead of a magnetic element in combination with a magnetic reed switch. Further instead of a mechanical reed switch any other proximity switch may be used as appropriate, for example an inductive or capacitive proximity switch. Such an inductive or capacitive proximity switch may further be used in combination with a magnetic element or a metal element. Further the skilled person will recognize that the magnetic element and/or the metal element may be formed of a compound comprising metal particles and one or more nonmetals, magnetic particles and nonmetals, or a combination of magnetic particles, metal particles and nonmetal particles. Furthermore the person skilled in the art will recognize the general possibility of reversing the location of the switch and the metal/magnetic element, although this is not preferred. For example an embodiment may be provided in which the switch is located in the cartridge and the magnetic/metal element is located in the device. In such an embodiment the cartridge may have an additional contact interface for connecting the switch with the device.

Figure 4:
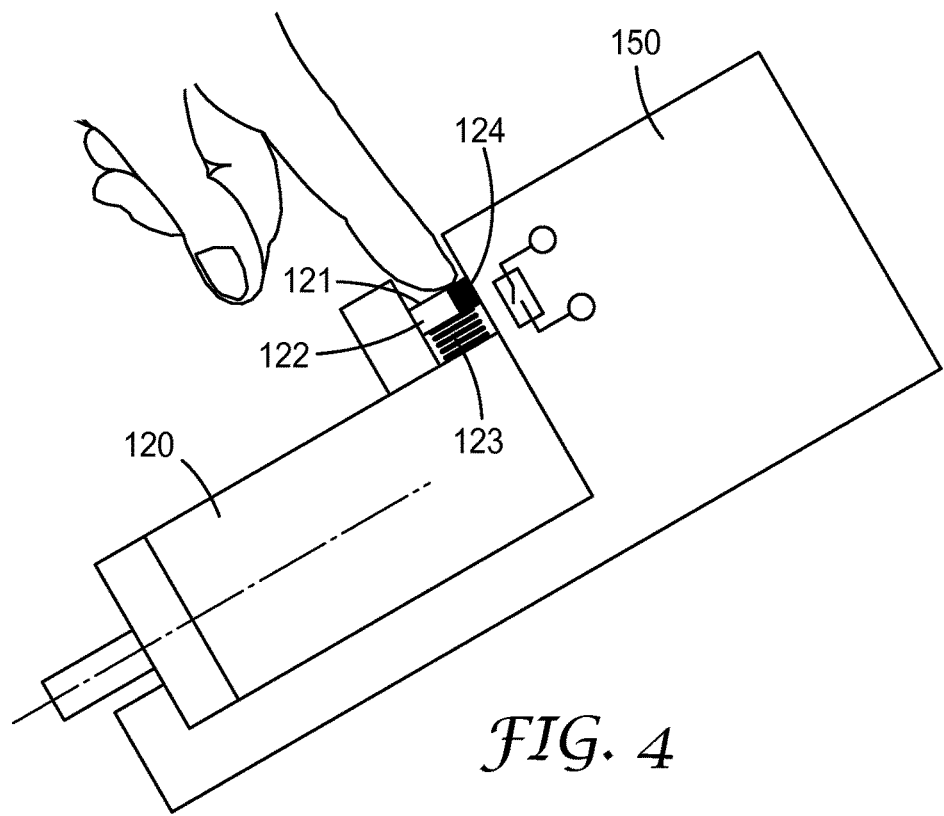
FIG. 4 is a schematic side view of the system of FIG. 3 in a mode of operation.
Figure 5:
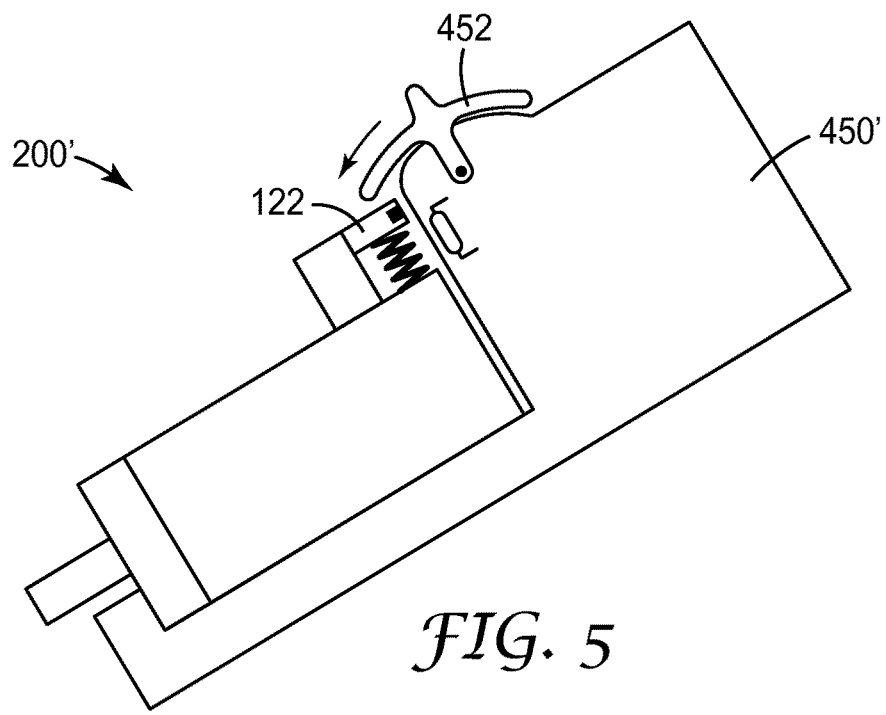
FIG. 5 is a schematic side view of a further system according to an embodiment of the invention.

FIG. 5 shows a system 200' which is identical to the embodiment shown in FIGS. 3 and 4 except for comprising an additional lever 452 arranged on the device 450'. The lever 452 is arranged such that a movement of the lever 452 causes the button 122 to move accordingly. In this example the additional lever forms the operating means although the cartridge may be used with an alternative dispensing device with the button 122 forming the operating means.

Figure 6:
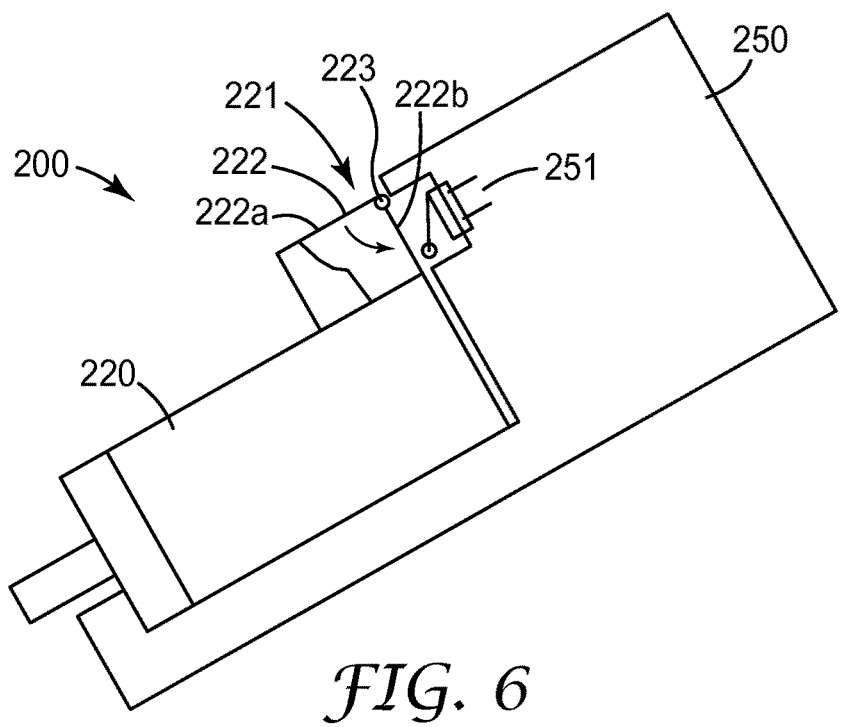
FIG. 6 is a schematic side view of a further system according to an embodiment of the invention.
Figure 7:
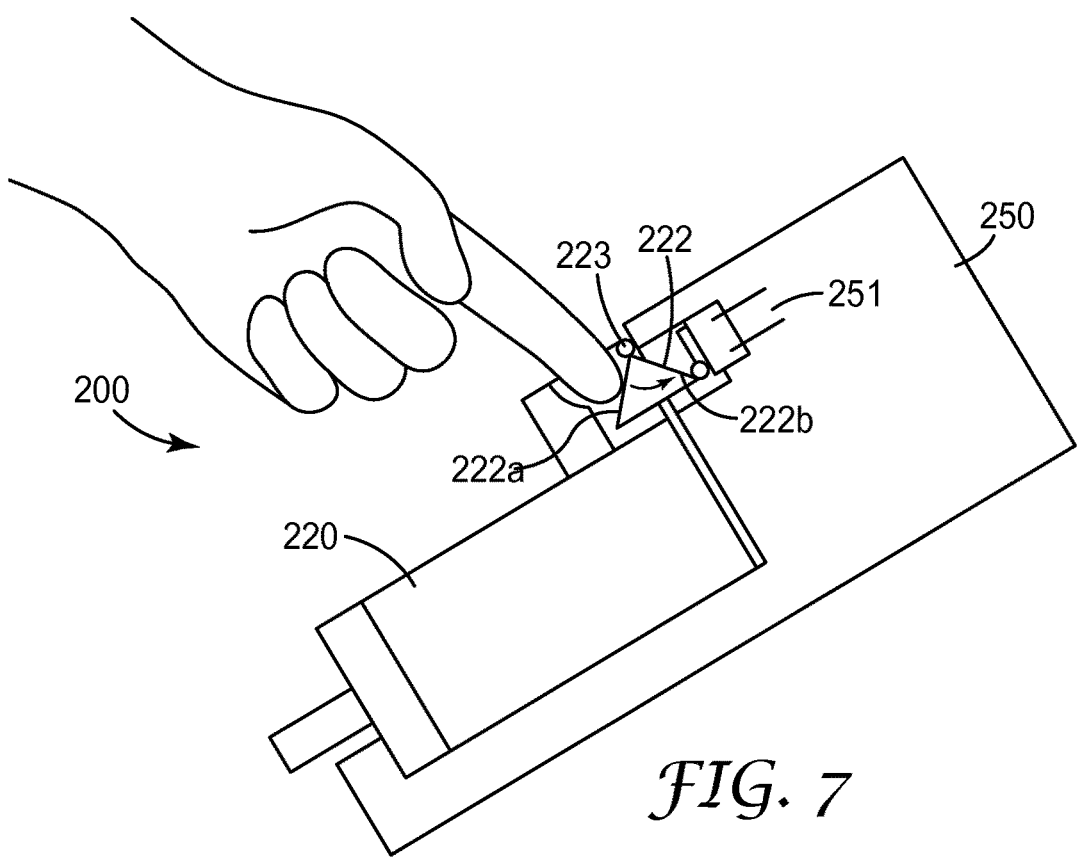
FIG. 7 is a schematic side view of the system of FIG. 6 in a mode of operation.

FIG. 6 shows a further example of a system 200 for dispensing a dental material having a device 250 and a cartridge 220. The cartridge 220 is removably placed in the device 250. The cartridge 220 has operating means 221 in the form of a pivotable lever 222. In the example the lever 222 is suspended in the cartridge by a pivot 223, and the lever 222 forms a first and a second lever arm 222a, 222b each extending away from the pivot 223. The lever 222 is arranged such that the first lever arm 222a is accessible for a user and such that the second lever arm 222b cooperates with a switch 251. Therefore actuating the first lever arm 222a (for example by a user pushing the first lever arm 222a down toward the cartridge as illustrated in FIG. 7) preferably causes the second lever arm 222b to operate the switch 251. In the example shown the switch 251 is a mechanical switch, for example a micro switch as typically used in electronics. However the skilled person will recognize that any switch which is adapted to close or interrupt an electric circuit or contact may be likewise used. Such a switch may for example have a light barrier which the second lever arm 222b interrupts or clears depending on the position to which the lever 222 is actuated. Further a proximity switch may be used which switches depending on the distance of the second lever arm 222b relative the proximity switch.

The lever 222 thus allows sensing a user input by a positioning of the first lever arm 222a. Further the lever 222 is adapted to transmit the user input to the second lever arm 222b by a corresponding positioning of the second lever arm 222b. Accordingly the lever 222 forms at least part of an interface for transmitting a cartridge output based on the user input to the operating means 221. The cartridge output in this example comprises a position of the second lever arm 222b. The cartridge output is variable. For example a first cartridge output may be based on a first position of the second lever arm 222b (shown in FIG. 6), and a second cartridge output may be based on a different second position of the second lever arm 222b (shown in FIG. 7). The first cartridge output may cause the switch 252 to deactivate in the first position and to activate the switch in the second position. The skilled person will recognize that the cartridge output may by based on additional positions, for example intermediate positions between the first and second positions or positions outside. Accordingly instead of a discrete on/off switch a control element may be used which is adapted to sense various positions of the second lever arm, for example within a generally continuous range of positions. The device 250 further has an interface for receiving the cartridge output. In the example the interface is at least partially formed by the switch 251.

In the example the two lever arms 222a, 222b are arranged in an L-shape. The L-shaped lever is arranged in the cartridge 220 such that one of the lever arms 222b extends into the cartridge 220 and the other one of the lever arms 222a forms a surface that is exposed at the outside of the cartridge 220. Other shapes of the lever are however possible.

Figure 8:
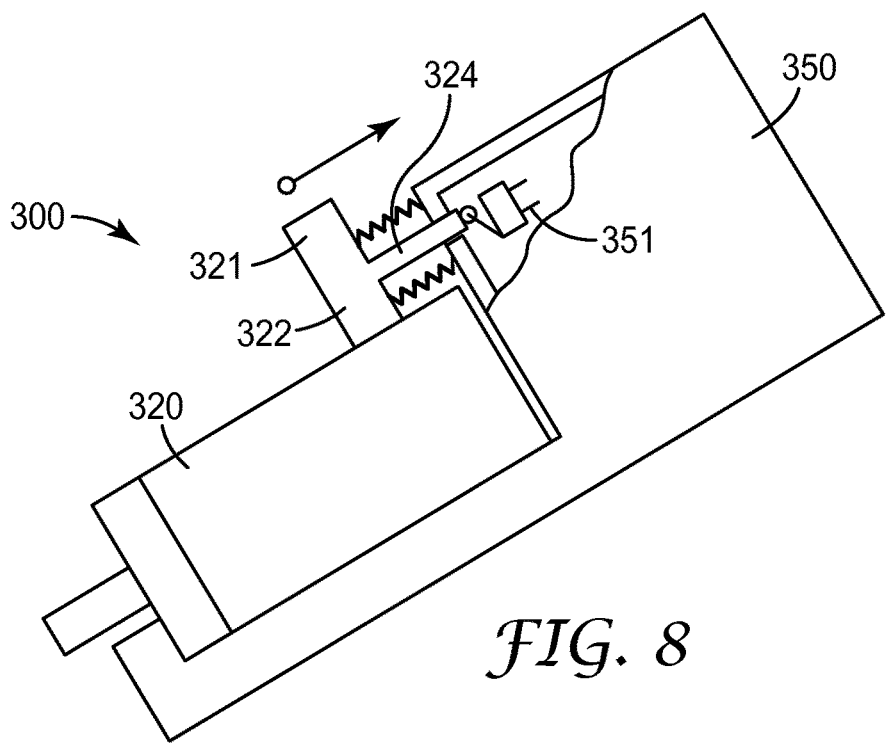
FIGS. 8-14 are schematic side views of further systems according to embodiments of the invention.

FIG. 8 shows a further example of a system 300 for dispensing a dental material. The system has a device 350 and a cartridge 320, latter being removably placed in the device 350. In this example operating means 321 is movably arranged at the cartridge 320. The operating means 312 has a button 322 with a push rod 324. The button 322 is arranged such that it is accessible for a user and such that the push rod 324 cooperates with a switch 351 in the device 350. Therefore actuating the button 322 (for example by a user pushing the button 322 toward the device 350) preferably causes the push rod to operate the switch 351. As described for the example in FIGS. 6 and 7 different types of switches may be used for selecting different modes of operation.

Further as in the example of FIGS. 6 and 7 a user input is sensed by a positioning of the operating means (in this example the button 322), and the operating means—a part of it or a part connected to it—forms at least part of an interface for transmitting a cartridge output based on the user input to the device 350. The cartridge output in this example comprises a position of the push rod 324.

Figure 9:
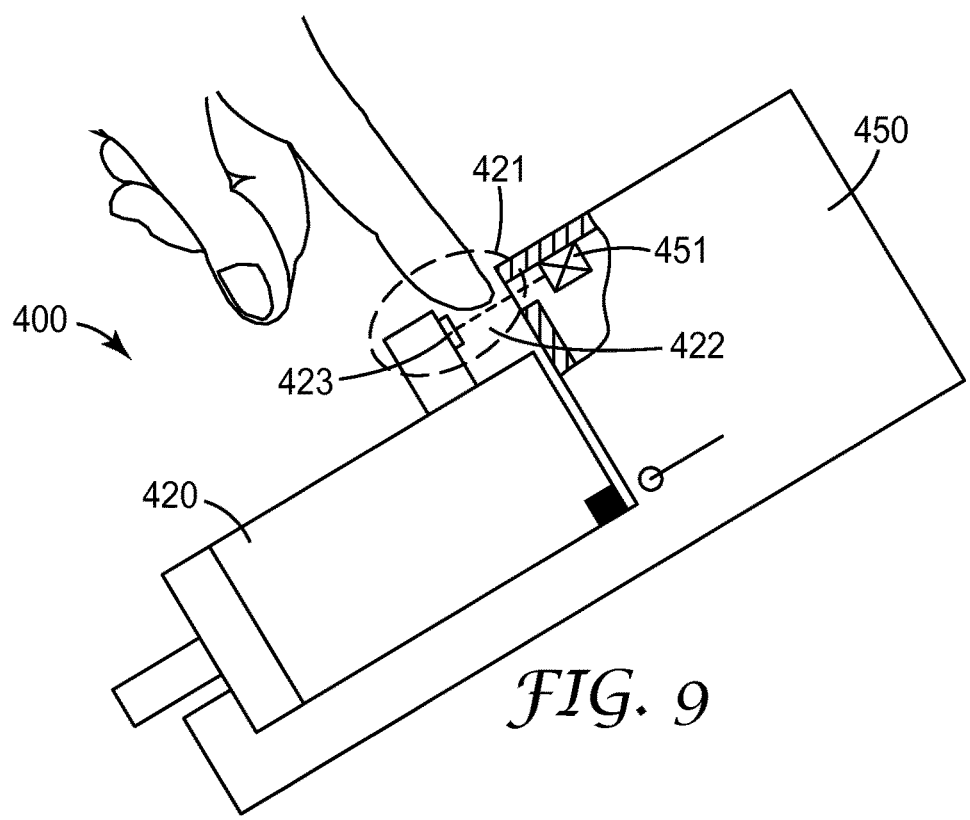

FIG. 9 shows a system 400 for dispensing a dental material. The system has a device 450 and a cartridge 420. In this example operating means 421 is formed by a finger space 422 and a reflector 423. The reflector 423 is arranged at the cartridge 420 to cooperate with a light sensor 451 in a situation in which the cartridge 420 is placed in the device 450. Further the operating means 421 the finger space 422 and the light sensor 451 in the situation in which the cartridge 420 is placed in the device 450 are arranged such that (appropriately) placing a finger in the finger space 422 interrupts a light ray sent from the light sensor 451 toward the reflector 423 and/or from the reflector 423 toward the light sensor 451. In this example the cartridge output is contactless, in particular an optical signal reflected from the reflector 423. The light sensor 451 is preferably adapted to provide an electric signal to circuitry for controlling the device.

Figure 10:
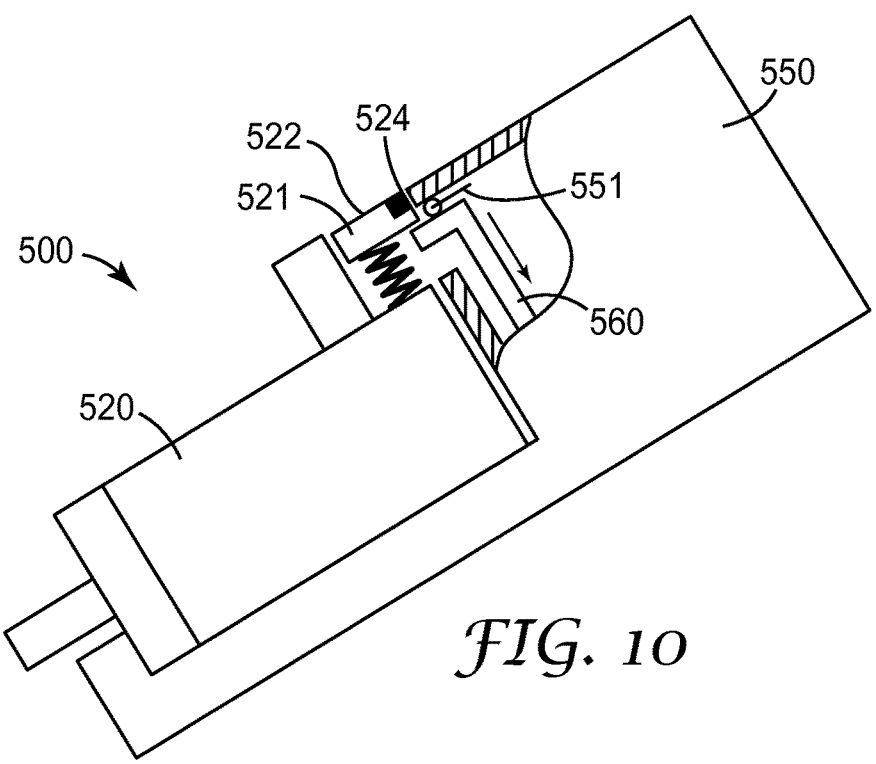

FIG. 10 shows a system 500 in which the cartridge interface comprises a combination of two different outputs. The cartridge 520 has operating means 521 which is functionally identical with the operating means shown in FIGS. 3 and 4. In particular the operating means has a button 522 which is mechanically coupled with a magnetic element 524 such that a movement of the button 522 also causes the magnetic element to move. The device 550 further has a reed switch 551 which is identical with the switch shown in FIGS. 3 and 4. Hence the cooperation of the operating means 521 and the reed switch 551 corresponds to the cooperation described in the example illustrated in FIGS. 3 and 4. In particular a movement of the button 522 causes the magnet element 524 to move relative to the reed switch 551 which in response switches depending on the position of the magnetic element 524 relative to the reed switch 551. The device 550 further has clutch member 560 which mechanically cooperates with the operating means 521 in a situation in which the cartridge 520 is placed in the device 550. In particular in the situation in which the cartridge 520 is placed in the device 550 the operating means 521 is mechanically coupled with the clutch member 560 so that moving the operating means 521 also causes the clutch member 560 to move. Thus the cartridge interface further provides a contact output or mechanical output in addition to the contactless output. The clutch member 560 in the example is connected to a clasp nut of a spindle drive (not visible). Accordingly actuation of the operating means 521 may cause switching an electric switch as well as engaging or disengaging the clasp nut and the spindle of a spindle drive.

Figure 11:
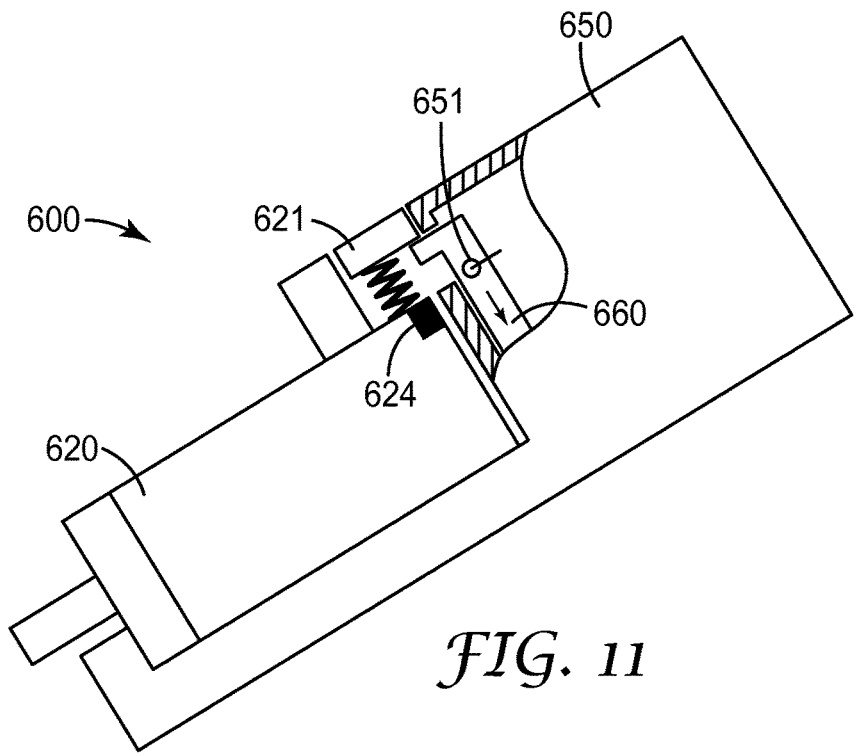

FIG. 11 shows a system 600 in which the cartridge interface comprises a further combination of two different outputs. The cartridge 620 has operating means 621 which is functionally identical with the operating means shown in FIGS. 3 and 4. In this example the device 650 has a reed switch 651 which is mechanically coupled to a clutch member 660 so that a movement of the clutch member 660 also causes the reed switch 651 to move. Further the clutch member 660 is mechanically coupled with the operating means 621 in a situation in which the cartridge 620 is placed in the device 650 so that moving the detecting member 621 also causes the clutch member 660 including the reed switch to move. The cartridge has a magnetic element 624 which is independent from the detecting member 621 and arranged at a fixed position at the cartridge. Accordingly moving the detecting member 621 causes the reed switch 651 to move relative to the magnetic member 624, and thus causes the reed switch 651 to switch depending on its position relative to the magnetic member 624.

Figure 12:
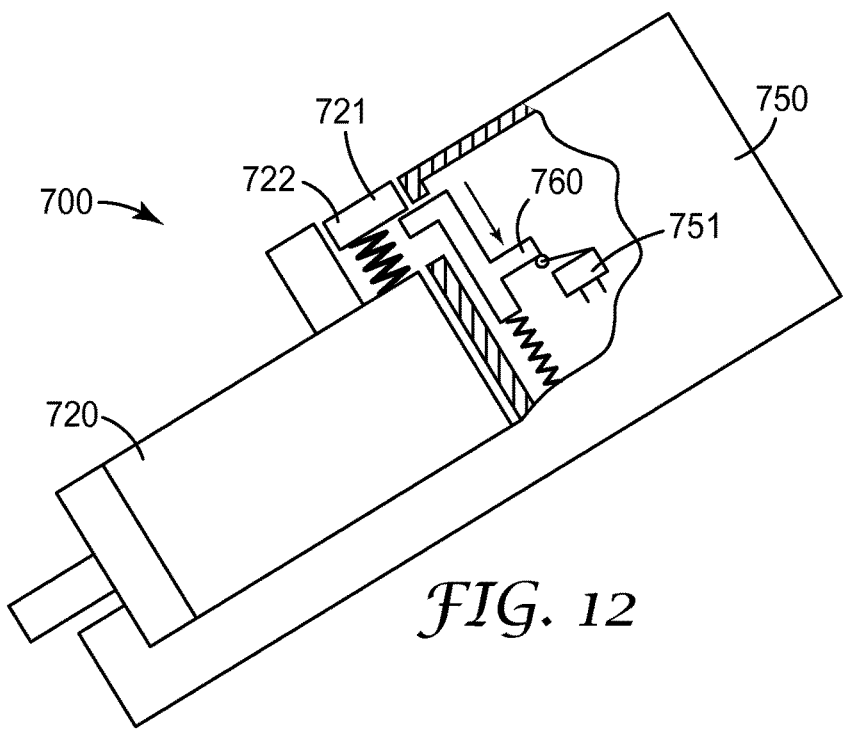

FIG. 12 shows a system 700 having a cartridge 720 which has operating means 721 which is movably suspended at the cartridge 720. The operating means 721 has a button 722 which is mechanically coupled with a clutch member 760 in a situation in which the cartridge 720 is placed in the device 750 so that moving the detecting member 721 also causes the clutch member 560 to move. The clutch member 760 further cooperates with a mechanical switch 751. In particular the clutch member 760 and the mechanical switch are arranged such that the switch 751 switches dependent on the position of the clutch member 760. Thus the cartridge interface further provides a contact output or mechanical output.

Figure 13:
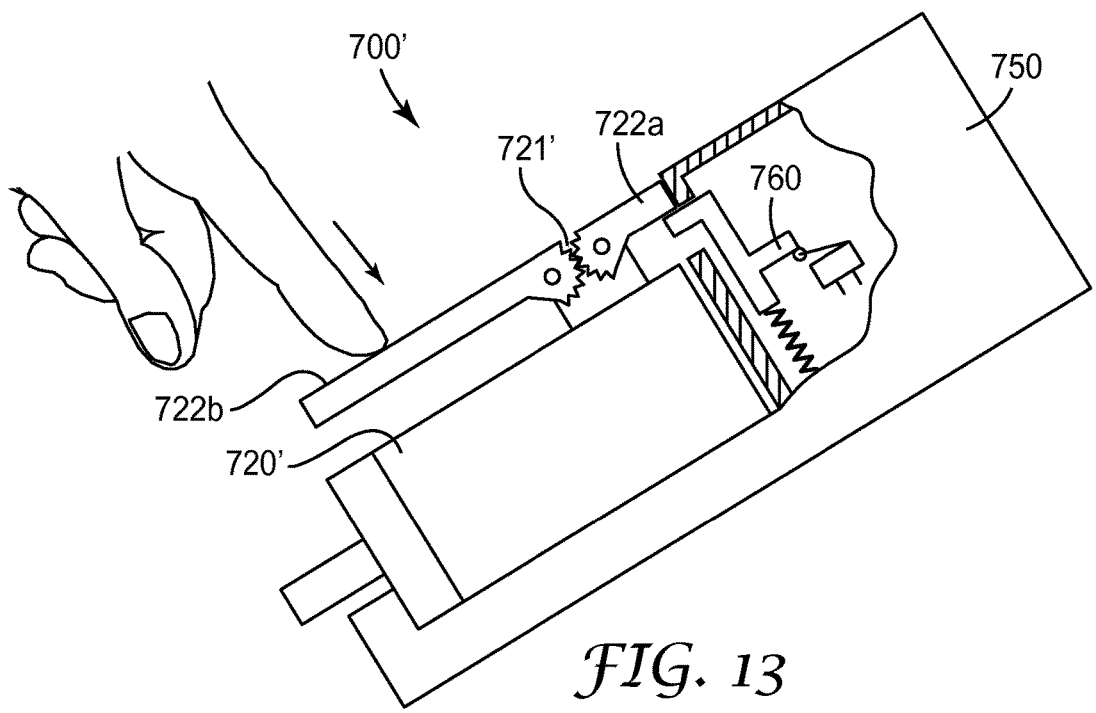

FIG. 13 shows a system 700' having the same device 750 as shown in FIG. 12 but a cartridge 720' with an alternative operating means 721'. The operating means 721' has a first pivotable lever 722a and a second pivotable lever 722b which are coupled by a geared connection such that moving the second pivotable lever 722b away from the cartridge causes the first pivotable lever 722a to move toward the cartridge. The first pivotable lever 722a in a situation in which the cartridge 720' is placed in the device 750 is mechanically coupled with the clutch member 760.

Figure 14:
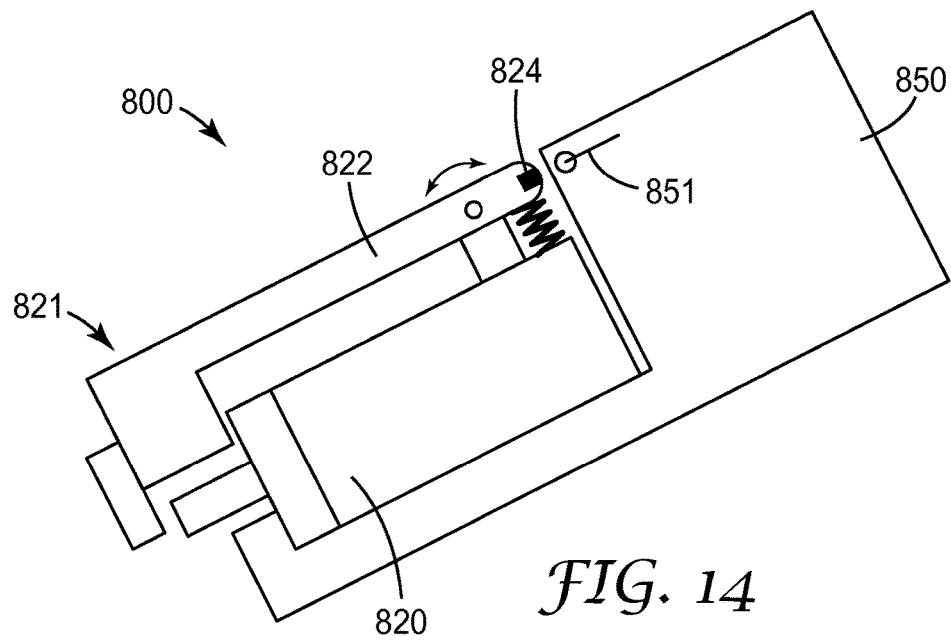

FIG. 14 shows a further system 800 having a cartridge 820 at which a operating means 821 is arranged in the form of a pivotable lever 822. The pivotable lever is pivotally suspended at a first end and has a free second end. The first end comprises a magnetic member 824 which rotates upon the lever rotates. A reed switch 851 in the device 850 accordingly switches depending on the rotational position of the lever 822.

Figure 15:
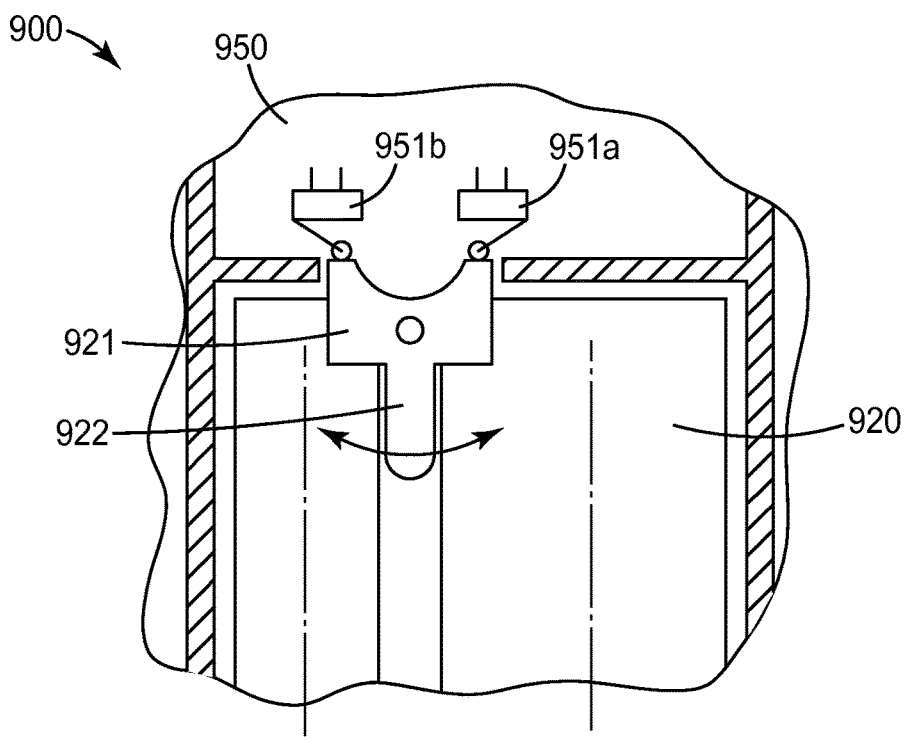
FIG. 15 is a schematic top view of a portion of a system according to an embodiment of the invention.

FIG. 15 shows a system 900 in which operating means 921 have a pivotable lever 922 which is mechanically coupled with two switches 951a, 951b such that a rotation of the lever 922 toward a first position activates switch 951a and a rotation toward an opposite second position activates 951b. Further a rotation of the lever 922 toward a first position deactivates switch 951b and a rotation toward the opposite second position deactivates 951a. The mechanical coupling between the lever 922 and the switches 951a, 951b is established in a situation in which the cartridge 920 is placed in the device 950. The system thus is adapted such that a selection between two different operation modes of the device is enabled by rotation of the lever toward the first or second position.

Figure 16:
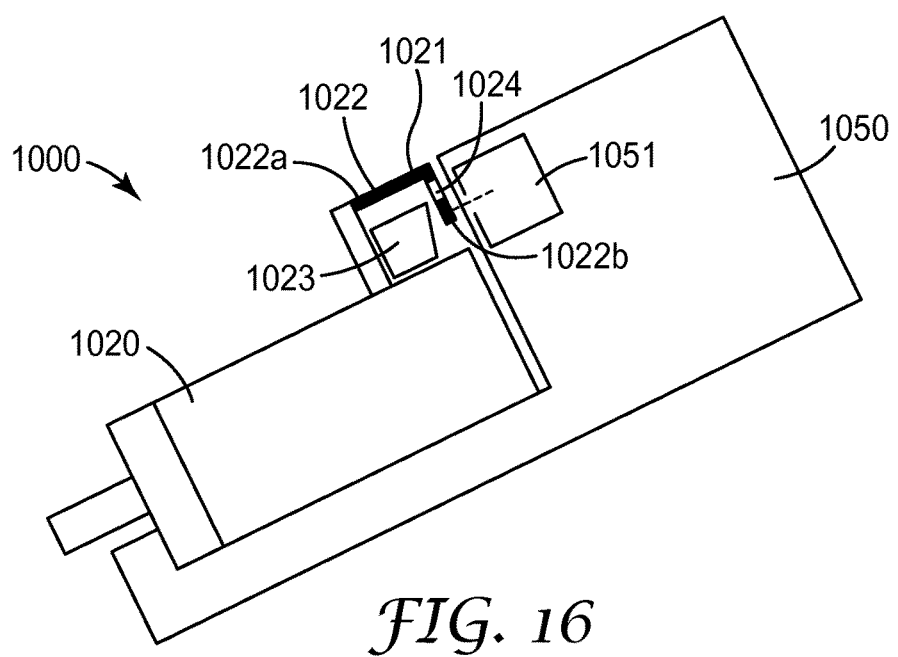
FIG. 16 is a schematic side view of a further system according to an embodiment of the invention.
Figure 17:
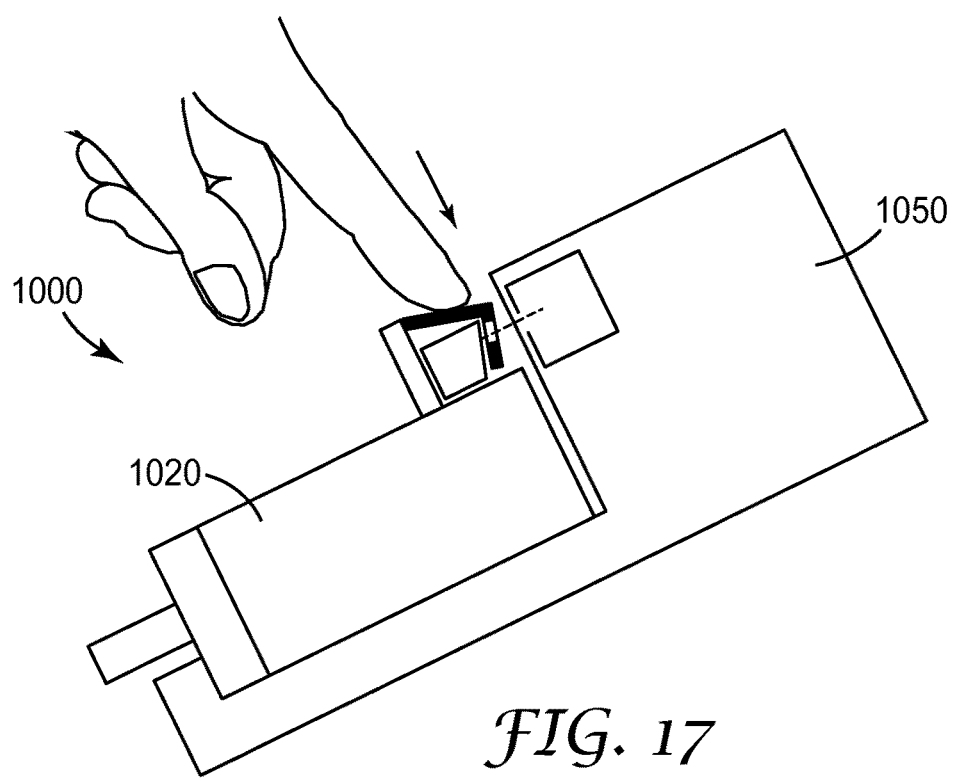
FIG. 17 is a schematic side view of the system of FIG. 16 in a mode of operation.

FIG. 16 shows a system 1000 having a device 1050 for dispensing dental material and a cartridge 1020. The cartridge 1020 has operating means 1021 which in the example are formed by a pivotable lever 1022. The lever 1022 has a first lever arm 1022a for receiving or detecting a user input and a second lever arm 1022b having a window 1024. The second lever arm 1022b is arranged between a mirror 1023 of the cartridge 1020 and an optical sensor 1051 of the device. Upon actuation of the lever 1022 between a first lever position (shown in FIG. 17), in which a user input is present, and a second lever position (shown in FIG. 16), in which no user input is present, the window 1024 moves between a first window position (FIG. 17) and a second window position (FIG. 16), respectively. In the first window position (FIG. 17) the optical sensor 1051 and the mirror 1023 can interact whereas in the second window position the line between the mirror 1023 and the optical sensor 1051 is blocked by the second lever arm 1022b. The optical sensor 1051 is preferably connected to circuitry which allows control of a function of the device in accordance to the optical signal sensed by the optical sensor 1051.

Figure 18:
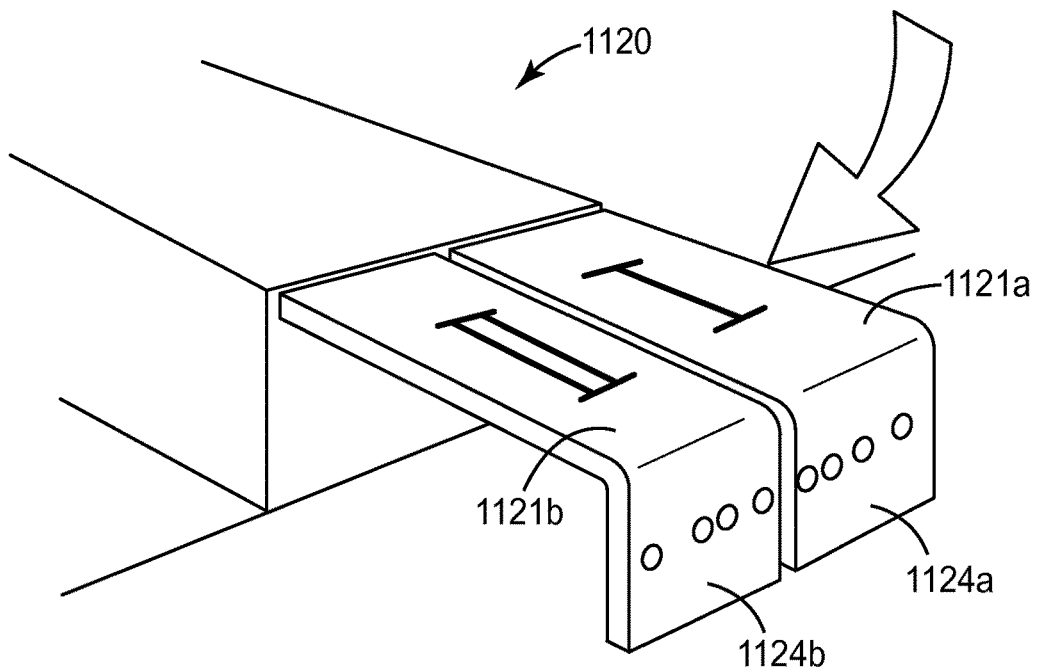
FIG. 18 is a perspective view of a portion of a further system according to an embodiment of the invention.

FIG. 18 shows a portion of a cartridge 1120 which has a first operating means 1121a and a second operating means 1121b. Each of the first operating means 1121a and the second operating means 1121b comprises an optical indicator 1124a, 1124b which, as shown, may comprise an encoding. The device (not shown) may have optical sensors which are adapted to recognize the encoding of the first operating means 1121a and the second operating means 1121b. The device may be further adapted to control one or more functions of the device depending on the encoding. For example the dispensing speed and/or the mixing speed may be controlled depending on the encoding. Thus different cartridges holding different dental materials may be used with the same device with the device automatically controlling its operation in a suitable manner for the particular dental material placed in the device.

The skilled person will recognize many variations of the above examples without departing from the invention. In particular different sensors and/or switches or combinations may be used. Further it will be clear to the skilled person that in all examples described herein the cartridge and the device are preferably separable, in particular that the cartridge is preferably removably placeable within a receptacle of the device. The in all examples the cartridge output transmitted to the device may be used to control one or more functions of the device. In a preferred embodiment the cartridge output may be used to activate and/or deactivate the device, in other words to switch the device on and/off for dispensing and/or for suspending dispensation of the dental material.

The invention claimed is:

1. A system for dispensing a dental material, comprising:
a cartridge from which the dental material is extrudable;
the cartridge comprising a contact based sensor for sensing a user input and for providing a cartridge output that is based on the user input sensed through the contact based sensor, wherein the cartridge output comprises a contactless signal;
and a dental dispensing device comprising:
a receptacle for receiving the cartridge and at least one piston for extruding the dental material from the cartridge; and
wherein the device includes a contactless sensor for detecting the contactless signal from the cartridge, and the device is configured to start the extruding of the dental material upon detecting via the contactless signal an activated position of the contact based sensor and to stop the extruding of the dental material upon detecting via the contactless signal an inactivated position of the contact based sensor.

2. The system of claim 1, wherein the contactless signal is encoded and the contactless sensor is configured to recognize the encoding.

3. The system of claim 1, wherein the device comprises at least one plunger and a drive for driving the plunger by motor power, the drive comprising a mechanical clutch which can be switched for selectively establishing or suspending a transmission between the motor and the plunger, and wherein the system is adapted such that the cartridge output can be further used to switch the clutch.

4. The system of claim 1, wherein the cartridge is removable from the receptacle.

5. The system of claim 1, further comprising a mixer, and wherein the cartridge includes separate containers for providing separate components and the components are extruded into the mixer for mixing the components.

6. The system of claim 1, in which the contact based sensor is a movable actuator.

7. The system of claim 6, wherein the movable actuator comprises a button.

8. The system of claim 6, wherein the movable actuator comprises a button and a lever, wherein movement of the lever causes movement of the button.

9. The system of claim 6, wherein the movable actuator comprises a pivotable lever.

10. The system of claim 6, wherein the movable actuator comprises a button with a push rod.

11. The system of claim 6, wherein the movable actuator comprises a pivotable lever having a first lever arm for receiving the user input and a second lever arm having a window.

* * * * *